United States Patent [19]

Wang et al.

[11] Patent Number: 4,584,408

[45] Date of Patent: Apr. 22, 1986

[54] PREPARATION OF 1,3-BIS(ARYLOXY)-2-PROPANOLS

[75] Inventors: Pen-Chung Wang, Midland, Mich.; James M. Renga, Walnut Creek, Calif.

[73] Assignee: The Dow Chemical Company, Midland, Mich.

[21] Appl. No.: 689,547

[22] Filed: Jan. 7, 1985

Related U.S. Application Data

[63] Continuation-in-part of Ser. No. 509,477, Jun. 30, 1983, abandoned.

[51] Int. Cl.[4] .................. C07C 41/16; C07C 43/26
[52] U.S. Cl. ................................. 568/48; 568/640; 568/643; 568/644
[58] Field of Search ................ 568/644, 48, 640, 643

[56]  References Cited

U.S. PATENT DOCUMENTS 3,056,762 10/1962 Tringali .................... 568/640 X
4,341,905  7/1982 Strege ...................... 568/640

FOREIGN PATENT DOCUMENTS 1028130 12/1958 Fed. Rep. of Germany .

OTHER PUBLICATIONS

Eimers (II), Chem. Abs., vol. 54 (1960) 14187(g).

*Primary Examiner*—Bernard Helfin
*Attorney, Agent, or Firm*—Paul Bork

[57]  ABSTRACT

Phenoxy resins and other 1,3-bis(aryloxy)-2-propanol compounds are prepared by contacting hydroxy-substituted aromatic compounds with organyl 2-oxo-1,3-dioxolan-4-ylmethyl carbonates.

21 Claims, No Drawings

PREPARATION OF 1,3-BIS(ARYLOXY)-2-PROPANOLS

CROSS-REFERENCE TO RELATED APPLICATION

This is a continuation-in-part of application Ser. No. 509,477, filed June 30, 1983 and now abandoned.

BACKGROUND OF THE INVENTION

The present invention relates to a novel chemical process. More particularly, the present invention relates to a process for preparing 1,3-bis(aryloxy)-2-propanol compounds including oligomeric and polymeric compounds containing 1,3-bis(aryloxy-2-hydroxy propylene functionality. The process is well suited to the preparation of this useful class of compounds, especially the above-defined class of phenoxy resins inasmuch as the process produces little or no salt by-products. Consequently, phenoxy resins prepared by the present process are especially suited for preparation of electronic components and for use in other applications where extremely low levels of ionic contaminants are desired.

Phenoxy resins are currently prepared in large volumes, most commonly by the glycidation of a bisphenol compound, especially bisphenol A, with epichlorohydrin in alkaline solution. Neutralization of the hydrochloric acid by-product results in the generation of large amounts of salt, the disposal of which may be expensive and enviromentally unacceptable. Furthermore, small amounts of such salt by-products unavoidably contaminate the resulting phenoxy resin making it extremely difficult to prepare cast objects with high dielectric properties.

It is previously known to prepare hydroxyalkyl derivatives of phenols or thiophenols by reaction of phenolic or thiophenolic compounds with cyclic organic carbonates in the presence of certain catalysts. In U.S. Pat. Nos. 4,341,905; 4,261,922; 4,310,707 and 4,310,708, the uses of alkali metal halides, stannates and phosphonium catalysts for this process are disclosed. Additional processes for preparing hydroxyethyl derivatives of phenols by the action of ethylene carbonate include the use of acids or bases disclosed in U.S. Pat. No. 2,448,767, potassium carbonate in U.S. Pat. No. 3,283,030 and alkali metal hydrides in U.S. Pat. No. 2,987,555. In U.S. Pat. No. 2,967,892, alkali metal hydroxides are disclosed as suitable catalysts for the reaction of phenols with chloromethylethylene carbonate.

SUMMARY OF THE INVENTION

According to the present invention 1,3-bis(aryloxy)-2-propanol compounds corresponding to the formula:

$$Ar(OX')_m$$

wherein
Ar is independently each occurrence an m valent aromatic moiety of up to about 30 carbons optionally containing heteroatoms;
m is independently each occurrence an integer greater than or equal to one; and
when m is equal to one, X' is —CH$_2$CHOHCH$_2$OAr, and when m is greater than one, X' is either hydrogen or —CH$_2$CHOHCH$_2$OX, and X is —Ar(OX')$_{m-1}$
are prepared by contacting a hydroxy-substituted aromatic compound corresponding to the formula Ar-(OH)$_m$, wherein Ar and m are as previously defined, with an organyl 2-oxo-1,3-dioxolan-4-ylmethyl carbonate corresponding to the formula:

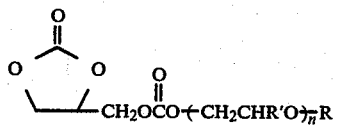

wheein R is lower alkyl or phenyl and n is a number from zero to about four, at an elevated temperature in the presence of a catalytically effective amount of an initiator.

The products are useful resins for preparation of coatings and solid objects. Monomeric products prepared by the present process are useful as plasticizers for plastics such as poly(vinylchloride), as photoinitiators and photosensitizers, and as intermediates for the synthesis of various drugs and agricultural products.

DETAILED DESCRIPTION OF THE INVENTION

The carbonate-containing reactant of the present invention is an organyl 2-oxo-1,3-dioxolan-4-ylmethyl carbonate. Such compounds have been previously described by C. F. Allpress et al., J. Chem. Soc., 2250 (1924). The compounds may be prepared by reaction of the chloroformic ester of the desired organyl group, —(CH$_2$CHR'O)$_n$R, with the sodium derivative of glycerol. Alternatively, the carbonates may be prepared in high yield in a salt-free process by reaction of a dicarbonate having as one substituent the organyl group —(CH$_2$CHR'O)$_n$R with 4-chloromethyl-2-oxo-1,3-dioxolane. The reaction proceeds rapidly at slightly elevated temperatures from about 25° C. to 150° C., optionally in the presence of a catalytically effective amount of an initiator such as a base or quaternary ammonium or phosphonium salt. The preferred method of forming the present starting reactants is the latter method inasmuch as no salt by-products are thereby formed.

Most preferred carbonate-containing reactants are methyl 2-oxo-1,3-dioxolan-4-ylmethyl carbonate and ethyl 2-oxo-1,3-dioxolan-4-ylmethyl carbonate. It is seen that use of the present carbonate reactants provides heretofore unrecognized advantages in that two aromatic substituents may be simultaneously introduced into the glycerol moiety, leading for the first time to a process capable of forming polymeric materials where polyhydroxy aromatic reactants are employed.

The hydroxy-substituted aromatic compounds for use in the present process include mono-, di- or polyhydroxy-substituted compounds. Monohydroxy aromatic compounds, e.g., phenols, lead to the preparation of monomeric 1,3-bis(aryloxy)-2-propanol derivatives. More particularly, such 1,3-bis(aryloxy)-2-propanols are of the formula ArOCH$_2$CHOHCH$_2$OAr.

Of much higher commercial interest are phenoxy resins and tris-phenoxy resins prepared from divalent or trivalent aromatic compounds, e.g., dihydroxy and trihydroxy aromatic compounds. These reactants lead to the preparation of products corresponding to the formula

and

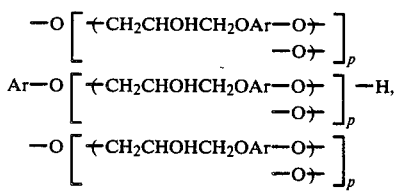

wherein p is a number representing the number of repeating units in the oligomer or polymer.

The tris-phenoxy resin is seen to contain trifunctionalized aromatic moieties able to impart branching to the molecule. Each branch may in turn lead to further branching ad infinitum until ultimately all chains terminate in hydroxyl functionality. In practice, the extreme steric hindrance resulting from the above branched structure generally prevents the above compounds to be prepared in extremely high molecular weights. More generally, a minor amount of trifunctional aromatic reactant may be added to mono- or difunctional phenolic compounds to introduce a limited amount of chain branching into the resulting compounds.

Preferably, the hydroxy-substituted aromatic compounds are bisphenols, dihydroxybenzenes or dihydroxybiphenyl compounds. As used herein the terms bisphenol and dihydroxybiphenyl are intended to signify compounds containing two phenylene moieties interconnected through an alkylene, substituted alkylene or heteroatom functionality in the case of bisphenol compounds, and directly bonded to one another in the case of dihydroxybiphenyl compounds. Particularly preferred are bisphenol A and p,p'-dihydroxybiphenyl or lower alkyl-substituted derivatives thereof.

While the products prepared by the present process are referred to herein as 1,3-bis(aryloxy)-2-propanols, e.g., compounds having —CH$_2$—CHOH—CH$_2$—functionality, the skilled artisan would be readily aware that reaction of the organyl 2-oxo-1,3-dioxolan-4-ylmethyl carbonate may also result in the concomitant formation of 2,3-bis(aryloxy)-1-propanol compounds, e.g., position isomers containing functionality of the formula:

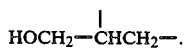

Inasmuch as both of the products are formed in the present process in an equilibrium distribution, reference to the product as a 1,3-bis(aryloxy)-2-propanol is also intended to include the corresponding 2,3-bis(aryloxy)-1-propanol compound.

The reaction is conducted in the presence of an initiator. Suitable initiators include acids, bases and salts. Examples of acidic materials include mineral acids, organic acids and solid acids such as Lewis acids, and acidic ion-exchange materials such as natural or artificial zeolites or organic ion-exchange materials. Basic catalysts include both organic and inorganic bases and basic ion-exchange materials. Salts include metal salts of acids such as metal halides, sulfate or bicarbonates and quaternary salts such as ammonium, sulfonium, sulfoxonium or phosphonium salts. Other suitable initiators are those compounds capable of forming in situ one or more of the above catalysts. Examples of the latter include amine or phosphine compounds capable of reaction to form ammonium or phosphonium salts.

More particularly, acid catalysts include sulfuric acid, hydrochloric acid, toluene sulfonic acid, potassium bisulfate, zinc chloride, aluminum chloride, and acid-exchanged resins of chlorinated (poly)styrene cross-linked with divinylbenzene or similar cross-linking substance. Basic compounds include amines such as pyridine, imidazole or triethylamine, and alkali metal hydroxides or carbonates. Salts include inorganic sulfate, nitrate, phosphate or halide salts or organic formate, acetate, benzoate, phenate or bisphenate salts of alkali metals, alkaline earth metals, metals of groups IB, IIB and VIII of the Periodic Table and ammonium, sulfonium, sulfoxonium or phosphonium quaternary ions. The latter class of ammonium or phosphonium quaternary ions are additionally described as follows.

Preferably, these salts have the general formula (R")$_4$AY where each R" is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate. The R" groups may be alkyl, aryl, alkaryl, aralkyl, or cycloalkyl. Also, two R" groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above.

Also, amine and phosphine salts such as tributylamine hydrochloride which are a form of quaternary salt will catalyze the reaction although these are generally less desirable in the reaction mixture.

The reaction is conducted at elevated temperatures selected so as to prepare acceptable amounts of the desired product in a reasonable time period. Suitably, reaction temperatures from about 100° C. to about 250° C. and preferably from about 150° C. to about 200° C. may be employed. The reaction is continued until substantially complete as evidenced by the cessation of carbon dioxide and hydroxyl containing by-product production. Generally reaction times from about one hour to several days are sufficient. In one embodiment of the invention, the by-product, a hydroxyl containing compound of the formula HO$+$CH$_2$CHR'O$)_n$R, is removed as it is formed, for example, by distillation if the boiling point thereof is sufficiently low. In this regard it may be advantageous to employ a reduced pressure or an inert sweep gas such as nitrogen to aid in removing the by-product. In another embodiment of the invention wherein HO$+$CH$_2$CHR'O$)_n$R is a higher boiling hydroxyl compound, particularly a glycol ether such as butoxyethanol, it is particularly beneficial to retain the by-product as a solvent for the resulting product, particularly where extremely viscous phenoxy resins are prepared.

Although any catalytic amount of the previously identified initiator compound may be employed, for practical reasons in batch operations, it is preferred to use about 0.1-10 mole percent of the initiator based on the hydroxy aromatic compound. Where it is desired to solubilize the catalysts, particularly the salt catalysts, a solubilizing agent such as a chelating agent, may additionally be employed according to known techniques in the art. Suitable chelating agents include crown ethers. Preferably, however, no solubilizing agent is added to the reaction. More initiator can be used but the excess confers little added advantage and may in fact be disadvantageous, particularly where the initiator is an electrolyte such as an alkali metal halide and high dielectric products are desired.

In a mode of the invention particularly adapted to continuous operation, one or more R" groups may be pendant methylene groups from a resin matrix so that the quaternary salt is a salt form of a strong base anion-exchange resin such as DOWEX® 21K, DOWEX® 11, DOWEX® MWA-1, or other such commercially available ion-exchange resins or the phosphonium equivalents of such quaternary ammonium-substituted resins. In such a continuous operation of the process, the mixed reactants are passed at an appropriate flow rate through a bed of the strong base anion resin maintained at a suitable temperature within the limits previously defined.

As previously mentioned, phenoxy resins prepared according to the present process may have very high dielectric strengths due to the relatively low amounts of initiator suitably employed and the ability to use nonhalide-containing initiators. Suitably, halide content of the phenoxy resins prepared by the present process is less than about 1000 ppm. Preferred are resins containing less than about 100 ppm and most preferably less than about 10 ppm halide contaminants.

Preferred initiators are alkali metal carbonate or halide salts and quaternary ammonium or phosphonium salts. Especially preferred are nonhalogen-containing quaternary ammonium or phosphonium salts that advantageously provide 1,3-bis(aryloxy)-2-propanols of extremely low halide ion and alklai metal ion contamination, e.g., less than 10 ppm halide ion concentration. Examples include ammonium or phosphonium carbonate, bicarbonate or acetate salts.

SPECIFIC EMBODIMENTS

Having described the invention, the following examples are provided as further illustrative and are not to be construed as limiting inasmuch as variations thereof will readily occur to the skilled artisan.

EXAMPLE 1

Preparation of 1,3-bis(phenoxy)-2-propanol

A mixture of 5.28 g (0.03 mole) of methyl 2-oxo-1,3-dioxolan-4-ylmethyl carbonate, 5.64 g of phenol (0.06 mole) and 0.07 g of anhydrous KF (0.0012 mole, 2 percent based on phenol) in a 100-ml round-bottom flask fitted with a mechanical stirrer and a distillation head is heated with stirring to 160° C. The progress of the reaction is monitored by $CO_2$ evolution or gas-liquid chromatography. After heating for about 4 hours, the reaction is discontinued and the product, 1,3-bis(phenoxy)-2-propanol, is isolated by distillation. The purified yield is 89 percent based on phenolic reactant.

EXAMPLE 2-10

The reaction conditions of Example 1 are substantially repeated employing the carbonate and phenolic reactants, reaction times and catalysts in the amount of 2 mole percent based on phenolic reactant further described in Table I. Results are contained in Table I.

TABLE I

| Example | Carbonate Reactant | Phenol | Catalyst | Reaction Time (hr) | Product (% yield)[1] |
|---|---|---|---|---|---|
| 2 | 2 | phenol | KF | 4 | 1,3-bis(phenoxy)-2-propanol (84) |
| 3 | 3 | phenol | LiCl | 8 | 1,3-bis(phenoxy)-2-propanol (91) |
| 4 | 3 | phenol | $(Bu)_4P^+Br^-$ | 8 | 1,3-bis(phenoxy)-2-propanol (82) |
| 5 | 3 | phenol | imidazole | 6 | 1,3-bis(phenoxy)-2-propanol (86) |
| 6 | 2 | phenol | LiCl | 8 | 1,3-bis(phenoxy)-2-propanol (88) |
| 7 | 2 | phenol | imidazole | 7 | 1,3-bis(phenoxy)-2-propanol (88) |
| 8 | 2 | m-cresol | KF | 4 | 1,3-bis(3-methylphenoxy)-2-propanol (80) |
| 9 | 2 | m-cresol | LiCl | 8 | 1,3-bis(3-methylphenoxy)-2-propanol (70) |
| 10 | 2 | 2,4-dcp[4] | KF | 8 | 1,3-bis(2,4-dichlorophenoxy)-2-propanol (70) |

[1] based on phenolic reactants
[2] ethyl 2-oxo-1,3-dioxolan-4-ylmethyl carbonate
[3] methyl 2-oxo-1,3-dioxolan-4-ylmethyl carbonate
[4] 2,4-dichlorophenol

EXAMPLE 11

Preparation of phenoxy resin

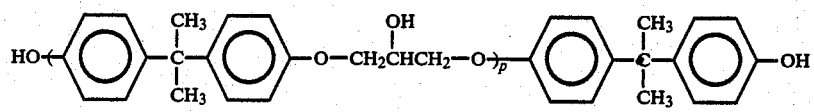

A mixture of 5.58 g (0.03 mole) of bisphenol A, 5.28 g (0.03 mole) of methyl 2-oxo-1,3-dioxolan-4-ylmethyl carbonate, 0.174 g (0.003 mole) of KF, and 5 ml of 2-(n-butoxy)ethanol is placed in a 50-ml resin pot equipped with a mechanical stirrer and a distillation head and warmed with stirring to 170° C. After heating at 170° C. for 4 hours, the gas evolution appeared to cease and the reaction mixture becomes viscous. The hot reaction mixture is poured into 8 aluminum cups and the solvent is evaporated in a vacuum oven (150° C.) for 24 hours to give 6.8 g (90 percent yield) of a yellow, brittle polymer with 12,000 molecular weight and m.p.=116° C. "p" can be calculated to be about 40. The above structure of the polymer is confirmed by nuclear magnetic resonance spectra data.

EXAMPLE 12

Preparation of low halide phenoxy resin

A mixture of 10.45 g (0.55 mole) of ethyl 2-oxo-1,3-dioxolan-4-ylmethyl carbonate, 11.4 g (0.5 mole) of bisphenol A, 1.85 g (0.05 mole) of triphenylbutylphosphonium bicarbonate and 10 ml of 2-(n-butoxy)ethanol is placed in a 50-ml resin pot equipped with a mechanical stirrer and a distillation head and warmed with stirring to 170° C. After heating at 170° C. for 6 hours, the gas evolution appears to cease and the reaction mixture becomes viscous. The hot reaction mixture is poured into 1 liter of methanol and the precipitated phenoxy resin is dried in a vacuum oven (150° C.) for 24 hours. The molecular weight of the resulting phenoxy resin is about 15,000 and both the chloride and sodium levels are below 10 ppm. "p" can be calculated to be about 50. The m.p. is 125°–127° C. and the Tg is 75° C.

EXAMPLE 13

When the reaction conditions of Example 11 are substantially repeated using 1 mole percent of triphenylbutylphosphonium acetate catalyst and a reaction time of about 6 hours, the resulting phenoxy resin has a molecular weight of about 7,000 and glass transition temperature, Tg, of 77° C. "p" can be calculated to be about 23. Chloride and sodium ion levels are less than 10 ppm.

EXAMPLE 14

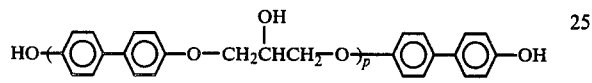

A mixture of 18.6 g (0. mole) of p,p'-dihydroxybiphenyl, 20.98 g (0.11 mole) of ethyl 2-oxo-1,3-dioxolan-4-ylmethyl carbonate, 2.06 g of triphenylbutylphosphonium bicarbonate and 20 ml of 2-(n-butoxy)ethanol is placed in a 50-ml resin pot equipped with a mechanical stirrer and a distillation head and warmed with stirring to 170° C. After heating at 170° C. for 6 hours, the gas evolution appears to cease and the hot reaction mixture is poured into 1 liter of methanol and the precipitated phenoxy resin is dried in a vacuum oven (150° C.) for 24 hours. The theoretical molecular weight of the resulting phenoxy resin is about 11,000 and both the chloride and sodium levels are below 10 ppm. "p" can be calculated to be about 43. The Tg is 62° C. Confirmation of the above structural formula for the product was made by nuclear magnetic resonance spectral data.

EXAMPLE 15

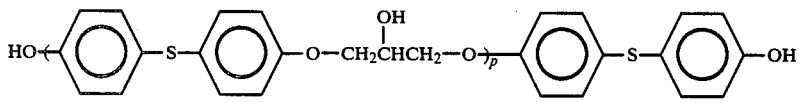

A mixture of 21.8 g (0.1 mole) of 4,4'-thiodiphenol, 20.98 g (0.11 mole) of ethyl 2-oxo-1,3-dioxolan-4-ylmethyl carbonate, 2.06 g (2.5 mole percent) of triphenylbutylphosphonium bicarbonate and 20 ml of 2-(n-butoxy)methanol is placed in a 50-ml resin pot equipped with a mechanical stirrer and a distillation head and warmed with stirring to 170° C. After heating at 170° C. for 6 hours, the gas evolution appears to cease and the reaction mixture is poured into 1 liter of methanol and the precipitated phenoxy resin is dried in a vacuum oven (150° C.) for 24 hours. The theoretical molecular weight of the resulting phenoxy resin is about 30,000 and both the chloride and sodium levels are below 10 ppm. "p" can be calculated to be about 95. The Tg is 77° C. Confirmation of the above product structure was made by nuclear magnetic resonance spectra.

EXAMPLE 16

A mixture of 7.6 g (0.04 mole) of ethyl 2-oxo-1,3-dioxolan-4-ylmethyl carbonate, 10.03 g (0.044 mole, 10 percent excess) of bisphenol A, 0.1 g of KF and 10 ml of 2-(n-butoxy)ethanol is placed in a 50 ml resin pot equipped with a mechanical stirrer and a distillation head and warmed with stirring to 170° C. After heating at 170° C. for 6 hours, the gas evolution appears to cease and the reaction mixture is poured into 6 aluminum cups and dried in a vacuum oven (150° C.) for 24 hours. The molecular weight of the resulting phenoxy resin is about 2,600 and the Tg is 72° C. "p" can be calculated to be about 8.

What is claimed is:

1. A process for preparing 1,3-bis(aryloxy)-2-propanol compounds corresponding to the formula:

$$Ar(OX')_m$$

wherein

Ar is independently each occurrence an m valent aromatic moiety of up to about 30 carbons;

m is independently each occurrence an integer greater than or equal to one; and when m is equal to one, X' is —CH$_2$CHOHCH$_2$OAr, and when m is greater than one, each X' is independently hydrogen or —CH$_2$CHOHCH$_2$OX wherein X is —Ar(OX')$_{m-1}$, comprising contacting a hydroxy-substituted aromatic compound corresponding to the formula Ar(OH)$_m$ wherein Ar and m are as previously defined, with an organyl 2-oxo-1,3-dioxolan-4-ylmethyl carbonate, corresponding to the formula:

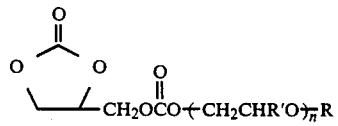

wherein R is lower alkyl or phenyl and n is a number from zero to about four, at an elevated temperature in the presence of a catalytically effective amount of an initiator.

2. A process according to claim 1 wherein the organyl 2-oxo-1,3-dioxolan-4-ylmethyl carbonate, is ethyl 2-oxo-1,3-dioxolan-4-ylmethyl carbonate, or methyl 2-oxo-1,3-dioxolan-4-ylmethyl carbonate.

3. A process according to claim 1 wherein the temperature is from about 100° C. to about 250° C.

4. A process according to claim 1 wherein the temperature is from about 150° C. to about 200° C.

5. A process according to claim 1 wherein the hydroxy-substituted aromatic compound is a bisphenol, dihydroxybenzene or a dihydroxybiphenyl compound.

6. A process according to claim 5 wherein the hydroxy-substituted aromatic compound is bisphenol A or p,p'-dihydroxybiphenyl.

7. A process according to claim 1 wherein in addition a solvent is present.

8. A process according to claim 7 wherein the solvent is a lower alkyl glycol monoether.

9. A process according to claim 8 wherein the solvent is 2-(n-butoxy)ethanol.

10. A process according to claim 1 wherein the initiator is an acid, base or salt.

11. A process according to claim 10 wherein the initiator is selected from the group consisting of mineral acids, organic acids, solid acids, organic bases, inorganic bases, basic ion-exchange materials, metal salts of acids and quaternary salts.

12. A process according to claim 11 wherein the initiator is an alkali metal halide or carbonate or a non-halogen-containing quaternary ammonium or phosphonium salt.

13. A process according to claim 1 wherein the initiator is present in an amount from about 0.1 to about 10 mole percent based on hydroxy-substituted aromatic compound.

14. The process of claim 1 wherein 1,3-bis(2,4-dichlorophenoxy)-2-propanol is prepared.

15. The process of claim 1 wherein a 1,3-bis(aryloxy)-2-propanol of the formula,

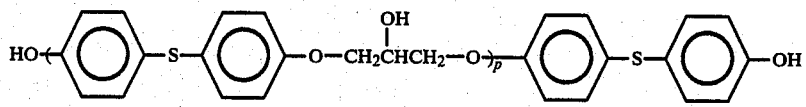

wherein p is a number representing the number of repeating units in the 1,3-bis(aryloxy)-2-propanol, is prepared.

16. The process of claim 1 wherein the initiator is selected from the group consisting of acids, bases and salts.

17. The process of claim 16 wherein the initiator is selected from the group consisting of mineral acids, organic acids and solid acids such as Lewis acids, acidic ion-exchange materials such as natural or artificial zeolites or organic ion-exchange materials, organic and inorganic bases, basic ion-exchange materials, metal salts of acids such as metal halides, sulfate or bicarbonates and quaternary salts selected from the group consisting of ammonium, sulfonium, sulfoxonium or phosphonium salts, amine or phosphine compounds capable of reaction to form ammonium or phosphonium salts.

18. The process of claim 16 wherein the initiator is selected from the group consisting of sulfuric acid, hydrochloric acid, toluene sulfonic acid, potassium bisulfate, zinc chloride, aluminum chloride, and acid-exchanged resins of chlorinated (poly)styrene cross-linked with divinylbenzene or similar cross-linking substance, pyridine, imidazole, triethylamine, and alkali metal hydroxides or carbonates, inorganic sulfate, nitrate, phosphate or halide salts or organic formate, acetate, benzoate, phenate or bisphenate salts of alkali metals, alkaline earth metals, metals of groups IB, IIB and VIII of the Periodic Table and ammonium, sulfonium, sulfoxonium or phosphonium quaternary ions.

19. The process of claim 18 wherein the initiator is selected from the group consisting of potassium fluoride, lithium chloride, tetrabutylphosphonium bromide, imidazole, triphenylbutylphosphonium bicarbonate and triphenylbutylphosphonium acetate.

20. The process of claim 1 wherein the 1,3-bis(aryloxy)-2-propanol compound is a phenoxy resin of the formula, HOArO—CH$_2$CHOCH$_2$OArO)$_p$H wherein p is a number representing the number of repeating units in the resin.

21. The process of claim 1 wherein the 1,3-bis(aryloxy)-2-propanol compound is a tris-phenoxy resin of the formula,

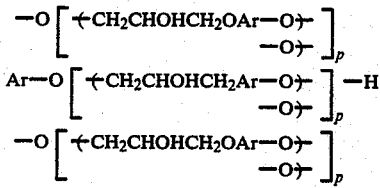

wherein p is a number representing the number of repeating units in the resin.

* * * * *